(12) United States Patent
Verstreken

(10) Patent No.: US 6,451,186 B1
(45) Date of Patent: Sep. 17, 2002

(54) IMMERSION SENSOR FOR MONITORING ALUMINUM ELECTROLYTIC CELLS

(75) Inventor: Paul Verstreken, Aarschot (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 09/517,862

(22) Filed: Mar. 3, 2000

(30) Foreign Application Priority Data

Mar. 5, 1999 (DE) .......................................... 199 09 614

(51) Int. Cl.[7] ................................................ G01N 27/26
(52) U.S. Cl. ...................... 204/400; 204/243.1; 205/775
(58) Field of Search ................................ 204/422, 423, 204/400, 243.1, 244–247, 247.3; 205/775

(56) References Cited

U.S. PATENT DOCUMENTS

| | | | |
|---|---|---|---|
| 3,380,897 A | * | 4/1968 | Dewey |
| 3,420,765 A | * | 1/1969 | Uhrenholdt |
| 3,546,086 A | * | 12/1970 | Sayles |
| 3,598,711 A | * | 8/1971 | Flais |
| 3,785,947 A | * | 1/1974 | Baldwin et al. |
| 3,914,169 A | * | 10/1975 | Horowitz |
| 4,098,651 A | * | 7/1978 | Alder |
| 4,105,507 A | * | 8/1978 | Von Krusenstierna et al. |
| 4,342,633 A | | 8/1982 | Cure |
| 4,639,304 A | | 1/1987 | Báder et al. |
| 4,814,062 A | * | 3/1989 | Redey et al. |

FOREIGN PATENT DOCUMENTS

| | | |
|---|---|---|
| DE | 25 03 635 A1 | 7/1975 |
| GB | 1 594 223 | 7/1981 |
| NZ | 176269 | 1/1977 |

OTHER PUBLICATIONS

Juan José del Campo[1], et al. A Decision Making Alrogithm For Potroom Operation, *Light Metals* (1995) Month Unavailable pp. 413–421.

J.M. Jolas, et al., Cathode Drop Comparisons On Aluminium Pechiney Modern Cells, *Light Metals* (1995) Month Unavailable pp. 403–411.

* cited by examiner

*Primary Examiner*—T. Tung
(74) *Attorney, Agent, or Firm*—Akin, Gump, Strauss, Hauer & Feld, L.L.P.

(57) ABSTRACT

An immersion sensor is provided for monitoring of aluminum electrolysis cells, together with a corresponding measurement arrangement and a measuring method. In order to obtain reproducible measurements, the bath electrode of the immersion sensor is arranged on a carrier.

12 Claims, 3 Drawing Sheets

IMMERSION SENSOR FOR MONITORING ALUMINUM ELECTROLYTIC CELLS

BACKGROUND OF THE INVENTION

The invention relates to an immersion sensor for monitoring of aluminum electrolysis cells with a bath (electrolytic) electrode. Furthermore, the invention relates to a measuring arrangement for monitoring electrolysis cells with a tank, as well as a measuring method using the measuring arrangement.

In the manufacture of aluminum in aluminum electrolytic cells, the functional capacity of such systems, in particular the electrolysis tank, is monitored. These tanks are essentially made of carbon. It is important to ensure that these carbon tanks do not have any leaks, thus for example, in the course of their operation they do not get any holes in them, through which the molten aluminum could flow out. For the purpose of this test, a suitable metal rod is pushed into the aluminum through the cryolite layer, which lies on the aluminum melt. The metal rod is connected via connection lines and a voltmeter to reference electrodes arranged in the tank bottom, such that the voltage incident between the metal rod (or the aluminum melt) and the reference electrode can be measured. A drop of this voltage indicates that the conductivity between the two electrodes is increasing. This in turn indicates that the tank layer arranged between the two electrodes is defective.

With this measuring method it has been determined that generally no reproducible measurements are possible. As a rule, with measurements carried out after each other, for example even at different locations of the electrolysis device, different voltages are measured. This can be attributed, among other things, to the fact that the thermal equilibrium in the immediate vicinity of the metal rod is sensitively disturbed by its immersion; due to the good heat conductivity of the metal rod and its relatively high heat capacity, cryolite solidifies on the rod. This leads to the creation of an insulation layer on the rod and consequently to a poor contact with the molten aluminum.

SUMMARY OF THE INVENTION

An object of the present invention, starting from the known state of the art, is to create a possibility for obtaining reproducible measurement results.

This object is achieved according to the invention for an immersion sensor in that the bath electrode is arranged on a carrier (support) having an immersion end. This carrier functions for the stabilization of the bath electrode, which for its part can have a very small mass, since the mechanical stability is ensured by the carrier, in order, for example, to allow the penetration of the cryolite layer. The bath electrode itself can thus have a very small heat capacity, so that the measurement vicinity is not influenced in any significant way. In particular, it is advantageous that the carrier be constructed as a carrier tube and preferably comprises an organic material. In particular, it can be made of cardboard. The organic material combusts very quickly upon immersion, at least at its surface, and causes a cleaning effect by the combustion gases in the immediate vicinity. Possibly adhering salt or cryolite is thus practically blown off, i.e. removed, from the carrier or from the bath electrode, respectively. On a carrier of this type a bath electrode can be arranged, preferably constructed as a wire with a diameter of approximately 0.05 mm to 5 mm, especially approximately 0.1 mm to 2 mm, without any significant heat capacity. The corresponding carrier tube made of cardboard also does not substantially affect the heat capacity of the aluminum melt. It has been shown that possible small quantities of solidified cryolite are melted again in a few seconds, so that reproducible measurement values are obtained. In particular, equivalent measurement results can be obtained with such sensors at different locations of the electrolytic cells.

In one expedient embodiment of the invention, the bath electrode is constructed to run partially within the carrier tube and to project out of the immersion end of the carrier tube, wherein the projecting part of the bath electrode is advantageously arranged at least partially on the outer wall of the carrier tube. It has thereby proven to be advantageous that the part of the bath electrode arranged outside of the carrier is at least partially surrounded by a flammable protective sheath, in order to prevent damage upon penetration of the cryolite layer. The carrier (1) can expediently have a refractory material on the immersion end, at least on its outer side.

Advantageously, the bath electrode is made of a metal, in particular of molybdenum or a tungsten-rhenium-alloy.

In one advantageous embodiment of the invention, an electro-chemical measuring cell and/or a thermo-element with two thermo-element legs is arranged at the immersion end of the carrier. In order to obtain a simple embodiment of the invention, it is expedient to connect the bath electrode with the thermo-element in an electrically-conducting manner. In particular, the thermo-element can be mounted in the immersion end of the carrier tube and be connected with two contacts of a connection piece for the purpose of the connection to signal lines. The bath electrode can thereby be connected in an especially simple embodiment to a contact of the connection piece, which means, for example, that an end of the bath electrode is welded to the contact of the connection piece.

The object is solved by an immersion sensor according to the invention for a measurement arrangement for the monitoring of aluminum electrolysis cells with a tank, wherein the bath electrode is connected via a signal line and a voltmeter to a reference electrode arranged on the outside of the wall of the tank or in the wall. Using this measurement arrangement, the measuring method according to the invention is characterized in that the immersion sensor is first dipped into the cryolite layer, that the temperature measurement of the cryolite occurs there, and that the immersion sensor is then immersed with the bath electrode into the liquid aluminum, and the voltage between the bath electrode and the reference electrode is measured. In particular, it can be advantageous that the voltage between the bath electrode and the reference electrode is measured in a state of thermal equilibrium.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
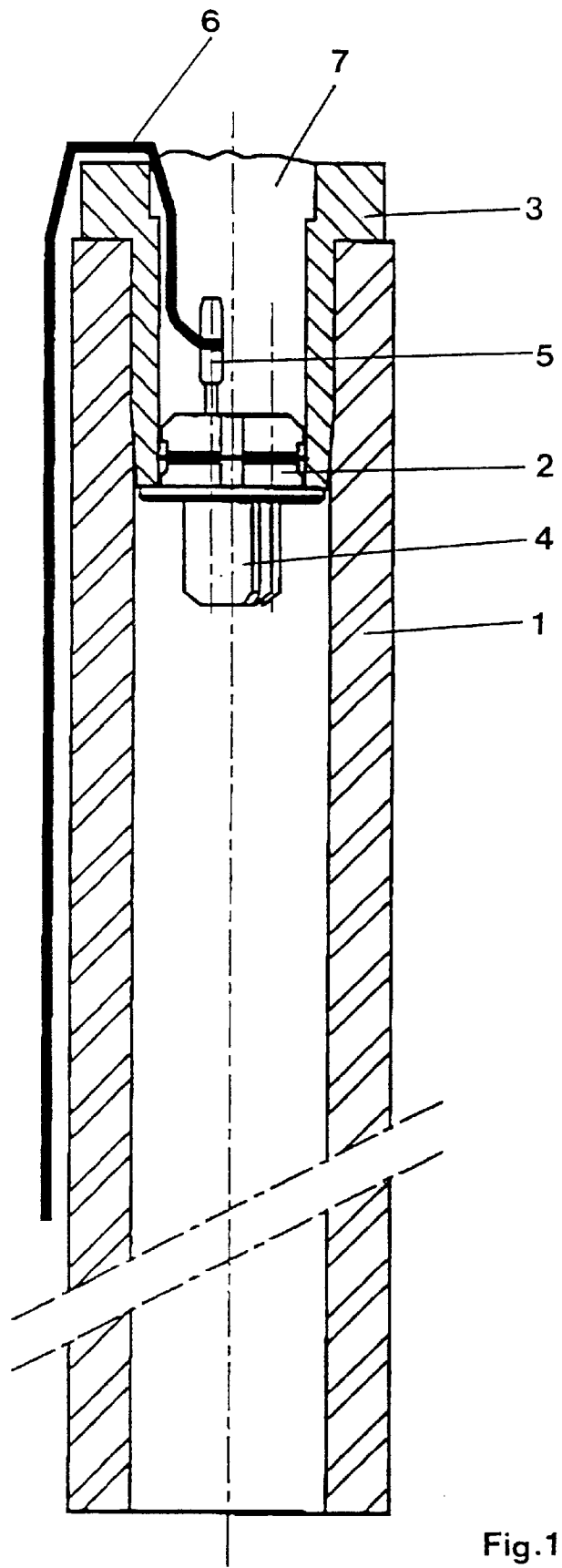
FIG. 1 is an embodiment of the immersion sensor according to the invention.

The immersion sensor represented in FIG. 1 has a carrier tube 1 made of cardboard. A connection piece 2 is arranged on its immersion end and is affixed using a refractory material 3. On its end facing away from the immersion end the connection piece 2 has connections for contacting a signal line, and on its immersion end has a contact 5 for connection of the bath electrode 6. The immersion end of the carrier tube 1 is closed with a cement 7 surrounding the contact 5.

The bath electrode 6 projects out of the carrier tube 1 and lies with its outer end on the outer side of the carrier tube 1. Prior to use, the outer part of the bath electrode 6 is at least partially protected by a cover (not shown in the drawing). The cover can, for example, be made of a paper winding. This cover combusts during the penetration of the immersion sensor through the cryolite layer and prevents a solidification of cryolite on the bath electrode 6.

Figure 2:
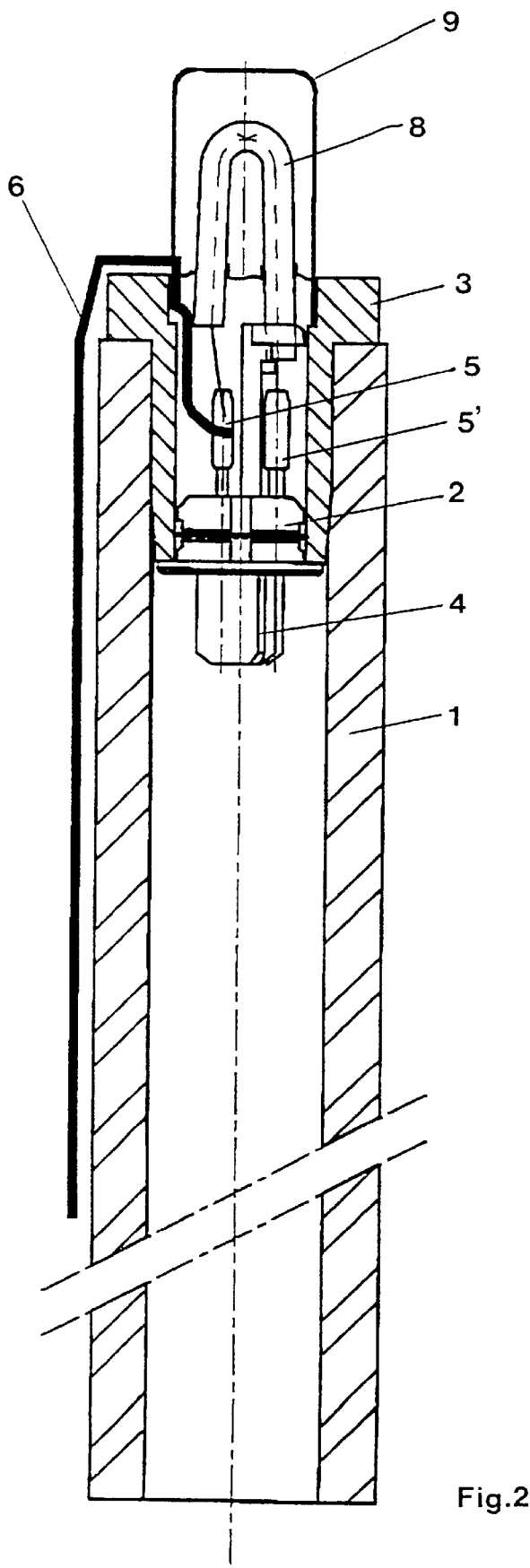
FIG. 2 is a further embodiment of the immersion sensor.

FIG. 2 shows another embodiment of the immersion sensor according to the invention. In this embodiment a thermo-element 8 is additionally arranged on its immersion end. This thermo-element 8 is protected by a protective cap 9 from the influence of cryolite. This protective cap 9 is made of a material which dissolves in the cryolite layer, for example. of aluminum. The thermo-element 8 is connected at the contacts 5, 5' to the connection piece 2, and from there, signal lines (not shown in the drawing) lead over the connections 4 to measuring devices. The bath electrode 6 is connected to the contact 5 of the thermo-element 8 and is connected to a signal device via the same signal line passing through the carrier tube 1.

Figure 3:
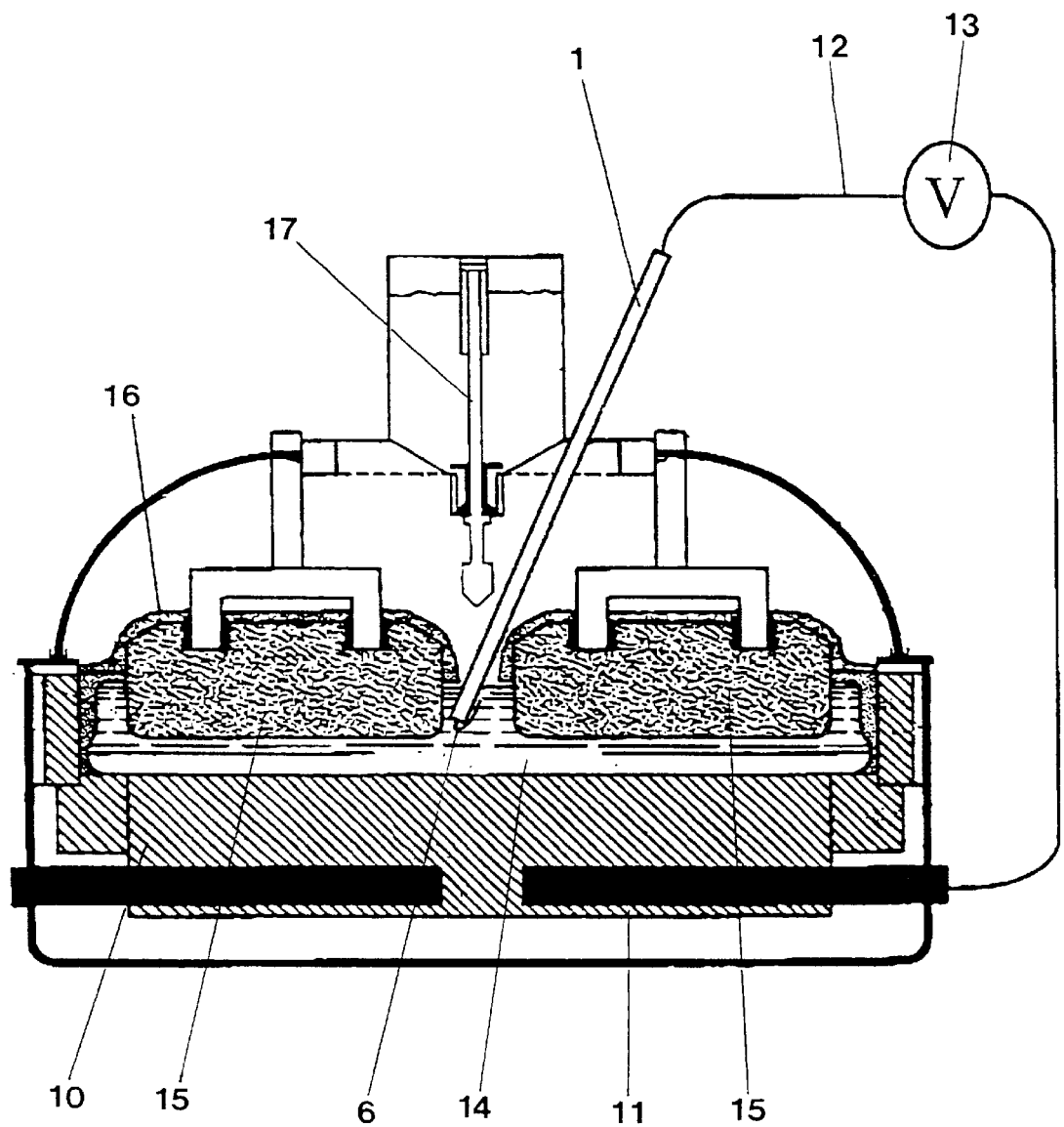
FIG. 3 is the schematic diagram of a measurement arrangement according to the invention.

FIG. 3 shows a measurement arrangement using the immersion sensor shown in FIG. 1 or 2. The electrolysis tank has a wall 10 made of carbon. In this wall 10 the reference electrode 11 is arranged, which is connected via signal lines 12 and a voltmeter 13 to the bath electrode 6. The reference electrode 11 forms at the same time one of the cathodes for the electrolytic process. The electrolysis bath 14 consists in its lower part of liquid aluminum and in its upper part of cryolite. The carbon anodes 15 project into the electrolysis bath 14 from above. These are partially encased by an aluminum oxide crust 16. To punch through the crust a so-called crust breaker 17 is provided, which makes possible a passage from above to the aluminum melt.

The immersion sensor can now be immersed first into the electrolytic bath 14 in order to measure the temperature. Then, it is immersed as far as the bottom of the electrolysis bath 14 in order to measure the voltage incident between the bath electrode 6 and the reference electrode 11. When the wall 10 of the tank is damaged by destruction of the graphite block forming the wall 10, the electrical resistance of the wall 10 drops, and a voltage drop is registered at the voltmeter 13. An advance warning thereby occurs when the wall 10 is damaged. Due to the small heat capacity of the bath electrode 6 constructed of a wire, no appreciable influence of the electrolysis bath 14 occurs. A solidification of bath components on the immersion sensor does not take place, so that reproducible measurements are possible even at different locations in the electrolysis bath.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. An immersion sensor for monitoring of aluminum electrolysis cells, comprising a bath electrode (6) arranged on a carrier tube (1) having an immersion end, wherein the carrier tube (1) comprises an organic material, wherein the bath electrode (6) runs partially within the carrier tube (1) and projects from the immersion end, wherein the part of the bath electrode projecting from the immersion end of the carrier tube (1) is arranged at least partially o an outside wall of the carrier tube (1).

2. The immersion sensor according to claim 1, wherein the organic material comprises cardboard.

3. The immersion sensor according to claim 1, wherein the carrier tube (1) has a refractory material on the immersion end, at least on its outer side.

4. An immersion sensor for monitoring of aluminum electrolysis cells, comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein the bath electrode (6) comprises a wire with a diameter of approximately 0.05 mm to 5 mm.

5. The immersion sensor according to claim 4, wherein the diameter of the wire is approximately 0.1 to 2 mm.

6. An immersion sensor for monitoring of aluminum electrolysis cells, comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein the part of the bath electrode (6) arranged on an outside wall of the carrier tube (1) is at least partially surrounded by a flammable protective sheath.

7. An immersion sensor for monitoring of aluminum electrolysis cells, comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein the bath electrode (6) comprises a metal selected from the group consisting of molybdenum and a tungsten-rhenium-alloy.

8. An immersion sensor for monitoring of aluminum electrolysis cells, comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein an electro-chemical measurement cell and/or a thermo-element (8) with two legs is arranged at the immersion end of the carrier tube (1).

9. The immersion sensor according to claim 8, wherein the bath electrode (6) is connected with the thermo-element (8) in an electrically-conducting manner.

10. An immersion sensor for monitoring of aluminum electrolysis cells, comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein a thermo-element (8) and/or an electrochemical measurement cell is mounted in the immersion end of the carrier tube (1) and is connected to signal lines via two contacts (5,5') of a connection piece (2).

11. The immersion sensor according to the claim 10, wherein the bath electrode (6) is connected to one of the contacts (5) of the connection piece (2).

12. A measurement arrangement for monitoring an aluminum electrolysis cell with a tank, comprising an immersion sensor for monitoring of aluminum electrolysis cells, the immersion sensor comprising a bath electrode (6) arranged on a carrier tube (1) having an immersion end, wherein the bath electrode (6) runs partially within the carrier tube (1) and projects from the immersion end, wherein the part of the bath electrode projecting from the immersion end of the carrier tube (1) is arranged at least partially on an outside wall of the carrier tube (1), and wherein the bath electrode (6) is connected via a signal line (12) and a voltmeter (13) to a reference electrode (11) arranged on an outside of a wall (10) of the tank or in the wall (10).

* * * * *